United States Patent [19]

Ford

[11] Patent Number: 4,661,526

[45] Date of Patent: Apr. 28, 1987

[54] CROSS LINKED POROUS MEMBRANES

[75] Inventor: Douglas L. Ford, New South Wales, Australia

[73] Assignee: Memtec Limited, New South Wales, Australia

[21] Appl. No.: 662,293

[22] PCT Filed: Jan. 26, 1984

[86] PCT No.: PCT/AU84/00015

§ 371 Date: Oct. 1, 1984

§ 102(e) Date: Oct. 1, 1984

[87] PCT Pub. No.: WO84/03054

PCT Pub. Date: Aug. 16, 1984

[30] Foreign Application Priority Data

Feb. 2, 1983 [AU] Australia ............................. PF7861

[51] Int. Cl.$^4$ ............................................. C08J 9/36
[52] U.S. Cl. ..................................... 521/53; 210/654;
210/500.38; 521/61; 521/62; 521/63; 521/64;
521/183

[58] Field of Search ............... 210/500.2, 654; 521/61,
521/62, 63, 64, 183, 53

[56] References Cited

U.S. PATENT DOCUMENTS 3,904,519  9/1975  McKinney, Jr. .................... 210/654

Primary Examiner—Morton Foelak
Attorney, Agent, or Firm—Oblon, Fisher, Spivak, McClelland & Maier

[57] ABSTRACT

A polymeric porous membrane having a matrix made from an aliphatic thermoplastic polyamide or from an aliphatic thermoplastic polyamide/polyimide copolymer which has both relatively non-crystalline and relatively crystalline portions. The pores in the membrane are defined by spaces between the relatively crystalline portions and at least some of the relatively crystalline portions are linked together by the reaction of a bisaldehyde with the membrane matrix.

28 Claims, No Drawings

CROSS LINKED POROUS MEMBRANES

FIELD OF INVENTION

This invention relates to porous membranes made from aliphatic thermo-plastic polyamides or aliphatic polyamide/polyimide copolymers.

BACKGROUND ART

Synthetic polymeric membranes are used for separation of species by dialysis, electrodialysis, ultrafiltration, cross flow filtration, reverse osmosis and other similar techniques. One such synthetic polymeric membrane is disclosed in Australian Patent Specification No. 505,494 of Unisearch Limited.

The membrane forming technique disclosed in the abovementioned Unisearch patent specification is broadly described as being the controlled uni-directional coagulation of the polymeric material from a solution which is coated onto a suitable inert surface. The first step in the process is the preparation of a "dope" by dissolution of a polymer. According to the specification, this is said to be achieved by using a solvent to cut the hydrogen bonds which link the molecular chains of the polymer together. After a period of maturation, the dope is then cast onto a glass plate and coagulated by immersion in a coagulation bath which is capable of diluting the solvent and annealing the depolymerised polymer which has been used. According to the one example given in this specification, the "dope" consisted of a polyamide dissolved in a solvent which comprised hydrochloric acid and ethanol.

In another membrane forming technique, the liquid material out of which the membrane is cast is a colloidal suspension which gives a surface pore density that is significantly increased over the surface pore density of prior membranes.

According to that technique a thermoplastic material having both relatively non-crystalline and relatively crystalline portions is dissolved in a suitable solvent under conditions of temperature and time which cause the relatively non-crystalline portions of the thermoplastic material to dissolve whilst at least a portion of the relatively crystalline portion does not dissolve but forms a colloidal dispersion in the solvent. The colloidal dispersion and solvent (i.e. the "dope") is then coated onto a surface as a film and thereafter precipitation of the dissolved thermoplastic portion is effected to form a porous membrane.

Membranes of both of the above kinds suffer from disadvantages which limit their commercial usefulness and applicability. For example, they exhibit dimensional instability when drying and may shrink by up to 7%. Thus, it is essential that they be kept moist prior to and after use. Furthermore, where the membranes are made from polyamide, it has not been possible to generate concentrated and varied chemical derivatives of the membranes and this restricts the situations to which the membrane may be applied.

Another disadvantage is that such polyamide membranes are fundamentally unstable and eventually become brittle on storage. The instability has been carefully investigated by I. R. Susantor of the Faculty of Science, Universitas Andalas, Padang, Indonesia with his colleague Bjulia. Their investigations were reported at the "Second A.S.E.A.N. Food Waste Project Conference", Bangkok, Thailand (1982) and included the following comments regarding brittleness:

"To anneal a membrane, the thus prepared membrane (according to Australian Pat. No. 505,494 using Nylon 6 yarn) is immersed in water at a given temperature, known as the annealing temperature, T in degrees Kelvin. It is allowed to stay in the water a certain length of time, calling the annealing time. For a given annealing temperature, there is a maximum annealing time, t(b) in minutes, beyond which further annealing makes the membrane brittle. Plotting 1n 1/t(b) versus 1/T gives a straight line. From the slope of this line it can be concluded that becoming brittle on prolonged annealing is a process requiring an activation energy of approximatey 10.4 kilocalories/mole. From the magnitude of this activation energy, which is of the order of van der Waals forces, the various polymer fragments are probably held together by rather strong van der Waals forces or hydrogen bond(s)."

We have confirmed that the brittleness is due to a recrystallization of water-solvated amorphous polyamide. In some cases (such as polyamide 6) brittleness occurs within 48 hours of immersion in distilled water (pH 7) at 80° C. Colorimetric —$NH_2$ end group analysis has shown that there is no significant hydrolysis of the amide groups during this time. As would be expected, the rate of embrittlement is catalysed by dilute acids (eg: pH of 1.0) due to nitrogen protonation and subsequent solvation. This effect explains the apparently low "acid resistance" of the polyamide membranes. However colorimetric determination of both —$NH_2$ end groups and —COOH end groups has shown that the effect is due to crystallization rather than acid catalysed hydrolysis.

There is a potential source of confusion in the use of words such as "acid-resistance" in the context of this specification. That most of the brittleness is due to physical effects rather than chemical decomposition or chemical solvation (at least for dilute acids) is shown by the extreme embrittlement caused on standing 5 minutes in absolute ethanol. The ethanol removes the plasticizing water tenaciously held by non-crystalline nylon as will hereinafter be described in relation to Example 2. Accordingly, the following definitions apply in this specification:

(a) "Embrittlement resistance" means hindrance or prevention of the physical recrystallization mechanism of the amorphous polymer matrix.

(b) "Acid-catalysed embrittlement resistance" means prevention of embrittlement of type (a) even in the presence of dilute acids (pH 1 to 7).

(c) "Acid solubility" means the rapid dissolution of polyamide in strong acids (100% formic acid or 6N hydrochloric acid).

(d) "Acid catalysed hydrolysis" means the scission of amide bonds (such scission is much faster in an amorphous polyamide than in a crystalline polyamide.)

As well as "embrittlement" the prior art membranes show the normal chemical defects of the parent nylon polyamides in that they possess only moderate oxidation resistance and bio-resistance.

It is an object of this invention to provide polymeric porous membranes composed of thermoplastic aliphatic polyamides (including polyamide/polyimide copolymers) which have greater resistance properties and improved mechanical stability than prior art membranes. It is a further object of the invention to provide polymeric porous membranes which readily lend themselves to the preparation of chemical derivatives thereof for particular uses.

DISCLOSURE OF THE INVENTION

According to one aspect of the invention there is provided a method of preparing a porous membrane comprising the steps of:

(i) dissolving an aliphatic polyamide or an aliphatic polyamide/polyimide copolymer which has both relatively non-crystalline and relatively crystalline portions into a solvent under conditions of temperature and time which cause the relatively non-crystalline portions of the polyamide or copolymer to dissolve while at least a part of the relatively crystalline portions of the polyamide or copolymer do not dissolve, but form a colloidal dispersion in said solvent, (ii) forming said colloidal dispersion and solvent into a film and thereafter causing precipitation of at least part of the dissolved non-crystalline portions in the film to form a porous membrane in which the pores are defined by spaces between the relatively crystalline portions, and, (iii) reacting the membrane with an aldehyde as herein defined to link at least some of the relatively crystalline portions with the aldehyde.

In the content of this specification the term "an aldehyde as hereindefined" means an aldehyde or aldehyde-yielding mixture in which the aldehyde functionality exceeds one —CH=O per molecule.

Preferably, the aldehyde is a bis-aldehyde and is selected from the group comprising glutaraldehyde, glyoxal, succindialdehyde, alpha-hydroxyadipaldehyde, terephthaldialdehyde and phthaldialdehyde as well as mixtures thereof. Furthermore, the aldehyde may be derived from a bis-aldehyde polymer, an acetal or an acetal ester.

The aldehyde reaction step may be controlled so that from 10% to 25% of the aldehyde chains are not linked at one end. In which case, the invention can include any one of the following steps of reacting at least some of the free ends of the single-link aldehyde chains with:

(i) a phenol that may be selected from the group comprising resorcinol, diphenylolpropane, tannic acid, pyrogallol, hydroquinone, metacresol and naphthol as well as derivatives or mixtures thereof.

(ii) a protein such as gelatin, (iii) a polyhydric colloid such as hydroxyethylcellulose The phenol modified chains may be further reacted with:

(a) sodium monochloroacetate in aqueous solution, or (b) aqueous diazonium salts Also, the phenol modified chains may be subjected to further processing including the steps of:

(a) reacting at least some of the remaining reactive single-link aldehyde chains with hydrazine, (b) reacting the phenolic hydroxyl groups with epichlorohydrin, (c) reacting the resultant epoxides with a diamine to fix a pre-determined concentration of amine groups hydrolysing excess epoxide groups to hydroxyls and, (d) reacting the amine groups with excess bis(isothiocyanate).

A membrane made in accordance with the method of the invention may be further treated by reacting it with sodium bisulphite, hydroxylamine-O-sulphonic acid or phenylhydrazinesulphonic acid. A phenol-modified membrane may be further reacted with a bis-aldehyde.

The invention also provides a polymeric porous membrane comprising a membrane matrix made from aliphatic thermoplastic polyamide or from a thermoplastic polyamide/polyimide copolymer which has both relatively non-crystalline and relatively crystalline portions and in which the relatively crystalline portions are joined together by relatively non-crystalline portions with pores in the membrane being defined by spaces between the relatively crystalline portions characterised in that at least some of the relatively crystalline portions are linked together by the reaction of an aldehyde as herein defined with the porous membrane matrix.

A particularly preferred bis-aldehyde is the five carbon atom glutaraldehyde which has the following formula:

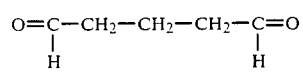

When polyamide 6 is used as the polymeric membrane, each low or relatively crystalline chain has a number of amide groups spaced apart along the chain and the bis-aldehyde (such as glutaraldehyde) displaces the hydrogen atom of the amide groups with their end carbon atom becoming bonded to the nitrogen atom in the polyamide chain as follows:

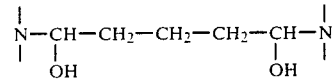

The glutaraldehyde provides a true cross link between the polyamide chains and this increases the membrane's bio-resistance as well as its embrittlement resistance.

In a modification of the invention, from 10 to 25% of the glutaraldehyde chains are not linked at each end to a polyamide chain but rather one end is unattached to leave the CH=O group in a more reactive form. This modification further improves the dimensional stability of the membrane and allows extensive chemical modification.

A feature of the glutaraldehyde type of cross-linking is that the permeability of the original polyamide membrane to water is unexpectedly only slightly and controllably affected as will be hereinafter apparent from example 2, although (as expected) the permeability of many dissolved solutes is greatly affected.

Further reaction with a phenol provides a membrane having acid-catalyzed embrittlement resistance. The resultant polyamide/phenol-aldehyde block copolymer is particularly useful in the treatment of effluent from food processing plants where alkaline mixtures are used as a cleaning agent, often after an acidic enzymatic cleaning treatment.

When the free end of the single-link aldehyde chain is reacted with a phenol (such as resorcinol) the free end of the aldehyde chain are transformed to bis(-phenylol)methane:

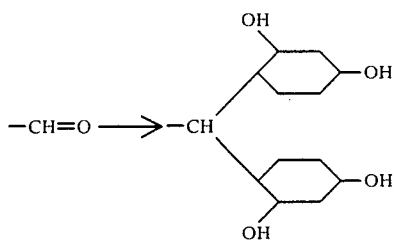

In addition to glutaraldehyde (or other bis-aldehyde) a small amount of formaldehyde may be used as the link particularly if free ends are reacted with resorcinol.

All or part of the glutaraldehyde can be replaced by equivalent amounts of many commercially available bisaldehydes such as glyoxal, succindialdehyde, alphahydroxyadipaldehyde, terephthaldehyde and phthaldialdehyde with very similar results including the preparation of chemical derivatives of the membrane arising from a proportion of end groups reacting as an aldehyde. Choice of bis-aldehyde depends largely on economic, safe-handling and aldehyde storage stability factors rather than chemical reactivity for most applications. Nevertheless some quite subtle differences such as absorption of colloids which can be important in commercial usage of the membrane may affect the choice of aldehyde.

The aromatic aldehydes are slower reacting, giving lighter-coloured products and are harder but more brittle. They also show the usual differences that aromatic aldehydes show from aliphatic aldehydes, eg: slower reaction with bisulphite.

Any desired properties likely to be needed in ultrafilters, ion-exchange resins, ion-specific resins, dyeing colour (by reaction with diazonium salts) or intermediates for highly active enzyme immobilization or affinity chromatographic surfaces can be obtained by choosing a cheap glyoxal, glutaraldehyde, succindialdehyde or terephthaldehyde and combining with a cheap reactive phenol such as resorcinol, diphenylolpropane, hydroquinone, pyrogallol, tannic acid or naphthol as well as mixtures or derivatives thereof. For specific purposes, specific phenolic derivatives can be used or the preferred glutaraldehyde/resorcinol treatment can be modified by simple soaking procedures in appropriate reagents.

A stable, sterilizable, controllably porous structure can be made by sequential reaction as in Example 6 with hydrazine, epichlorohydrin, hexamethylene-diamine and 1,4-phenylenebisisothiocyanate. This is excellent for reaction with the —NH$_2$ end groups of many proteins, whilst still allowing bioactivity and affinity chromatography for harvesting anti-bodies. The protein bond is covalent and stable but on a suitably long arm on an extended controllable interior structure.

In contrast thereto, a glutaraldehyde treated polyamide may be made electrically conductive by treatment with 4-phenyhydrazine-sulphonic acid to provide an electrodialysis membrane when the porosity is almost zero to a hydraulic pressure difference as in Example 3.

The reactivity of products containing highly reactive aldehyde groups is not restricted to phenols, although the latter are preferred for long-lived and aggressive environments. For example, protein, gelatin or hydroxyethylcellulose can be reacted with the membrane to give products which are very elastic and rubbery in ethanol. Furthermore, the preferred properties of the glutaraldehyde/resorcinol treated membranes can be combined with free aldehyde group reaction versatility by reacting once again with a bis-aldehyde to give an enhanced free aldehyde content. The product is then a polyamide/glutaraldehyde/resorcinol/bis-aldehyde which can form more concentrated and more stable derivatives. There is some advantage in using glyoxal for the last bis-aldehyde to give highest concentrations of —CHO. However, glutaraldehyde seems best for initial reaction with the polyamide, presumably for steric reasons of cross-linking.

Of course it is possible to involve the use of small quantities of the cheap mono-aldehyde, formaldehyde, at various stages to dilute the bis-aldehyde. However for steric reasons formaldehyde is undesirable for cross-linking in the initial polyamide reaction. Formaldehyde can have some use for a further diluent reaction with phenols. However, it is preferable to condense the formaldehyde separately with the phenols to make controlled pure reagents or condensation products and then to condense these with the polyamide/glutaraldehyde precursor.

DESCRIPTION OF PREFERRED EMBODIMENTS

Example 1

A solvent (A) was prepared by mixing 225 ml of 6.67N hydrochloric acid with 15 ml of anhydrous ethanol. 90 grams of 55 dtex 17 filament polyamide 6 with zero twist (which constitutes the polyamide starting material) was added to solvent A held at a temperature of 22° C. over a period of less than 15 minutes.

The dope of the polyamide 6 and solvent A was then left to mature for 24 hours at a temperature of 22° C. during which the relatively non-crystalline portions of the polyamide dissolved as did no more than 50% of the relatively crystalline portions of the polyamide 6 with the remaining relatively crystalline portion dispersing in the solvent.

After maturation, the dope was then spread as a film of about 120 micron thick on a clean glass plate. The coated plate was placed in a water bath where precipitation of the dissolved portions of the polyamide was effected within 3 minutes. The membrane was then reacted with 5% of glutaraldehyde (based on the dry membrane weight) at a pH of 3 to 6 at a temperature of 60° C. overnight. It was found that 50% to 80% of the glutaraldehyde had reacted depending upon the pH and that of these percentages 10% to 25% of the glutaraldehyde had one aldehyde free for further reaction.

Example 2

The polyamide 6 membrane made according to Example 1 had a water permeability of 339 liters/square meter/hour and rejected 81% of the protein in a standard edible gelatin. 60 grams of this membrane were treated with 2.24 grams of glutaraldehyde in 138 grams of water at pH 5.5 and at a temperature of 20° C. for 1 week followed by water washing. It was found that the membrane had reacted with 2.7% of its dry weight of glutaraldehyde. Of this 2.7%, about 0.62% (ie: 23% of glutaraldehyde reacted) was still reactive as an aldehyde. The water permeability was now 384 liters/square meter/hour and the gelatin rejection was 82%. These differences from the original permeability and gelatin rejection figures are very slight for any practical use.

The cross-linked membrane was not "acid-catalysed embrittlement resistant" as it became brittle in 6 days at 60° C. at pH 1 but was unaffected in 35 days at 60° C. at pH 13 (alkaline). There was a complete absence of traces of terminal —NH₂ groups, originally present in the polyamide 6 membrane of Example 1, as shown by the disappearance of the original yellow reaction with D.A.B.I.T.C. reagent, 4-dimethyl-aminophenylazobenzene-isothiocyanate. The slowed "acid-catalysed embrittlement" is due to the slow reversible reactions which yield glutaraldehyde and the starting polyamide 6. Such reactions are due to the acid-labile group,

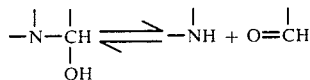

Also there will be present some proportion of acid-labile glutaraldehyde polymers. Confirmation of this reversibility was shown by the reaction of the membrane of this Example 2 with M/400 2,4-dinitrophenyl-hydrazine (DNP) in N/100 HCl at 22° C. In 21 hour 15% of the total glutaraldehyde had reacted with and removed from solution an equivalent of DNP; in 37 hour 17.4% and after 48 hour at 60° C., 23%. The reaction of glutaraldehyde with primary amides —CO—NH₂ has been well studied and the products are said to be stable reactive gels for affinity chromatography; see P. Monsan, G. Puzo and H. Mazarguil, Biochemie, 57, p1281 (1975). Reaction of polyamides containing secondary amide —CO—NH with glutaraldehyde could be expected to give less stable products.

Despite the low "acid catalysed embrittlement resistance" of the above polyamide 6/glutaraldehyde reaction product it was found to be a key intermediate in the preparation of preferred stable, tough, rubbery ultrafilter membranes by reaction with resorcinol (see Example 5) and of stable tough, rubbery oil and detergent repelling ultrafilters by reaction with gelatin or hydroxyethylcellulose (see Example 7). The reaction with gelatin in Example 7 illustrates the method of immobilizing an enzyme and for preparing absorbents for affinity chromatography. Many useful chemical derivatives can be prepared by known procedures and are described in examples below.

The brittleness of the membranes of examples one and two air dry (70% Relative Humidity) wet and in ethanol are indicated by the extension to break on stretching and by behaviour on rubbing in the following tables:

| MEMBRANE - EXAMPLE 1: | | | |
|---|---|---|---|
| | Air Dry | Wet | Ethanol |
| Extension to Break | 10% | 60% | 20% |
| Behaviour on rubbing | Rubbery | Rubbery | Powdered |

| MEMBRANE - EXAMPLE 2 | | | |
|---|---|---|---|
| | Air Dry | Wet | Ethanol |
| Extension to Break | 6% | 60% | 20% |
| Behaviour on rubbing | Rubbery | Rubbery | Powdered |

Thus, the glutaraldehyde to this stage has altered the chemical rather than the elastic properties (which appear identical). The large elastic improvement on further reaction is shown in later examples.

Example 3

5 g. of polyamide 6 yarn was dissolved in 15 g. of 98% formic acid to form a "dope" which was cast at 22° C. onto a sheet of high density polyethylene and dried at 60° C. for 10 hours to give a translucent film which was impermeable to water at 200 kpa at a thickness of 120 microns. The sheet was washed for 48 hours in distilled water and cut to a disc of 45 mm diameter. Wedging between metal plates showed a resistance of 200,000 ohms and only traces of weakly acidic groups, COOH, by methylene blue absorption.

Heating with 25% weight, volume glutaraldehyde at 100° C. for 48 hours and washing gave a translucent brown disc, with an unchanged resistance of 200,000 ohms but staining an intense purple in Schiff's fuchsin reagent, indicating the presence of many —CHO groups.

Heating at 60° C. in 2% sodium 4-phenylhydrazine-sulphonate and long washing gave a brown disc of lowered electrical resistance, 20,000 ohms showing the presence of conducting ionic groups. Methylene blue then gave an intense blue stain which would not wash out, showing large amounts of SO₃-groups. The product was satisfactory for an electrodialysis membrane, permeable to cations. Although ion-exchange properties were shown, the capacity and exchange rates were too low for commercial use. Similar results were obtained using films formed by precipitating a 98% formic acid "dope" by immersion in water. Contrary to the hydrochloric acid "dopes", a porous ultrafilter was not formed, as the 98% formic acid had dispersed the polyamide 6 molecularly, including the crystallites.

Example 4

To 90 g. of the dry polyamide 6 yarn used in Example 1 were added 0.9 g of isophthaloylchloride in 180 ml of cyclohexane and 3 g. of anhydrous potassium carbonate at 22° C. for 36 hours when 93% of the acid chloride had reacted as determined by the fall in UV absorption at 290 nanometers and the content of chloride reactable with boiling ethanolic silver nitrate in the cyclohexane. The cyclohexane was allowed to evaporate, the fibre washed in water for 1 hour, soaked to pH 3 in dilute HCl, washed overnight and dried at 60° C. The isophthaloyl chloride had largely converted some of the amide groups to imide groups with very little —COOH as determined by comparison of methylene blue absorption with the original yarn.

A "dope" was made up according to Example 1. The "dope" was slightly more turbid than that of Example 1 which indicated some greater content of colloidal crystallite or some cross-linking of amorphous polyamide. The "dope" was cast in parallel with the "dope" of Example 1. A comparison of the porous membranes formed showed that the permeabilities to water at 100 kPa for the unmodified polyamide 6 was 117 liter/square meter/hour whereas the imide modified membrane was 97 liter/square meter/hour The polyamide 6/isophthaloylimide-modified membrane above was reacted with glutaraldehyde as in Example 2 with little significant difference from the unmodified polyamide 6 membrane. This similarity extended to the further reaction with resorcinol according to Example 5. It is clear that the reacting species is the —CO —NH— group and that the imide group —CO —N= is not reactive and merely a diluent whose utility is largely restricted to forming a desired physical porous structure. Polyamide 6,6 also reacted as polyamide 6 but was somewhat less resistant to oxidation and to biological attack.

Example 5

12 grams of the glutaraldehyde cross-linked membrane of Example 2 were heated with 12 milliliters of a 1% aqeous resorcinol solution at pH 3.0 at a temperature of 60° C. for 12 hours and then washed. The resultant membrane had incorporated about 0.2% of its dry weight of the resorcinol. It was then dyed with p-nitrobenzenediazonium fluoroborate solution. It was not soluble in 6N hydrochloric acid in 1 hour whereas such acid rapidly dissolved precursor membranes. The resultant water permeability of 299 liter/square meter/hour and gelatin rejection of 75% showed that this further modification of the glutaraldehyde membrane occurred without significant change in permeability.

However the "embrittlement resistance" was raised to a high level—no embrittlement occurred even after 6 months at 60° C. at pH 7 as against 9 days for the embrittlement of the membrane before reaction with resorcinol. The extension to break (dry) was raised from 6% to 10% and the behaviour to rubbing remaining very rubbery; the extension to break (wet) was raised from 60% to 70% and the behaviour to rubbing was extremely rubbery whilst the extension to break in ethanol was raised from 20% to 30% with full rubber-like resistance to rubbing.

This membrane made by sequential glutaraldehyde then resorcinol treatment was apparently unaffected by two bio-resistance tests:
a. Enzymatic. A commercial mixture of papain and amylase was renewed weekly at 25° C. to 35° C. for 13 months and a prior art membrane stored therein remained intact but tore easily. In this respect it behaved better than one stored in water since "crystallization embrittlement" was hindered by the contained proteins, presumably because proteins are strongly absorbed and could be expected to hinder crystallization. The treated membrane remained very strong, tough and rubbery for the 13 months.
b. Compost Burial. The membranes were soaked in a commercial compost containing added commercial "Organic Compost Accelerator" for 13 months at 25° C. The untreated polyamide 6 membrane still showed reasonable strength but was not comparable to the apparently unchanged tough rubbery nature of the Example 5 membrane. A membrane made from polyamide 6,6 rather than polyamide 6 but otherwise treated according to Examples 2 and 5 showed poor bio-resistance to compost and easily broke up. Outstandingly good bio-resistance (to enzymes and compost) was also shown by membranes treated with glutaraldehyde according to Example 2 and then:
(a) reacted with hydrazine at pH 5.0 for 10 hours and washed or
(b) reacted with excess 2,4-dinitrophenylhydrazine in N/100 HCl overnight, then washed.

The glutaraldehyde/resorcinol treated membranes of Examples 5 are preferred for ultrafiltration purposes and as a stable matrix of controllable porosity from which chemical derivatives for ion-exchange or enzyme immobilization of affinity chromatography can readily be made as described in Example 6.

Repetition of the reactions but substituting hydroquinone, tannic acid or 2-naphthol-3,6-disulphonic acid for resorcinol gave analogous products showing expected properties. For example, the tannic acid product formed dark blue-black ferric derivatives; the naphthol-disulphonic acid derivative showed cation-exchange properties. None was physically superior, nor more convenient in ultrafilter manufacture than resorcinol. It is relatively certain that any commercial bisaldehyde/reactive phenol sequence will cross-link and stabilize against "embrittlement" due to amorphous polyamide recrystallization but glutaraldehyde has overall advantages as a reactant, although further reaction will provide tough, or more rubbery products.

Example 6

The membrane of Example 5 (1 g) was freed of trace —CHO groups by reaction with dilute hydrazine at pH 3.5 at 80° C. for 15 minutes and washed well. The resultant membrane was treated with 0.45 g epichlorohydrin in 10 ml 95% ethanol at pH 10 to 12 by adding 0.5 ml 2N NaOH at 80° C. and then washing well. The presence of combined epoxy-groups was demonstrated by slow precipitation of AgIO3 on adding AgIO4 in 2N HNO3. The epoxide was reacted with 1% aqueous hexamethylenediamine or 1% diethylenetriamine by heating to 80° C. for 30 minutes and then washed well. The presence in both cases of bound —$NH_2$ groups was shown by colorimetric estimation with p-dimethylaminophenylazobenzene-4-isothiocyanate. The products were then heated to 80° C. with excess 1% alcoholic 1,4-phenylenebisisothio-cyanate when the —$NH_2$ groups were converted to the yellow 4-isothiocyanotophenylthioureas (1). The isothiocyanato-end groups were estimated colorimetrically by reaction with 5-aminofluorescein to give the salmon-coloured derivative. Throughout the entire sequence the membranes retained their desirable ultrafiltration characteristics. The desirable isothiocyanate intermediates (1) may be regarded as polyamide/(imide)/aldehyde/polyphenol/epoxy/diamine/thioureaphenylisocyanates. They are dimensionally stable, controllable-porosity structures with ability to be heat sterilized. They are especially preferred for reaction with the free —$NH_2$ groups of proteins to give immobilized enzymes or affinity chromatographic column supports.

Example 7

The polyamide 6/glutaraldehyde membrane of Example 2 after drying at 60° C. reacted readily with 0.5% aqueous gelatin, draining, then heating in an oven at 60° C. for 15 hours. The product was fully "embrittlement resistant" and had an extension to break of over 50% in absolute ethanol (versus 20% without gelatin) and was fully rubbery. The membrane showed some utility in rejecting fine oil droplets when used as a cross-flow ultrafilter on oil emulsions in water. Similarly substitution of high molecular weight hydroxyethylcellulose for gelatin gave equivalent membranes which were "embrittlement resistant" and rubbery in ethanol with much the same utility in filtering oil emulsions.

Example 8

The glutaraldehye in Examples 2,3,5,6 and 7 was replaced with glyoxal, succindialdehyde, phthaldialdehyde and terephthaldehyde. There was little difference in behaviour but the products from terephthaldehyde tended to be too hard for ultrafilters, although the hardness could be turned to useful account when powdered high-pressure liquid affinity chromatographic packings were needed. The aromatic bis-aldehydes tended to be rather slow in reaction but always gave lighter-coloured products. The reactivity of all intermediates was in line with the properties of the parent aldehydes eg: polyamide 6/aliphatic bis-aldehydes gave membranes which contained —CHO groups readily reacting with $NaHSO_3$ (stained by Schiff's reagent) whereas the aromatic bis-aldehydes reacted slower. However, all formed 2,4-dinitro-phenylhydrazones, as expected.

The use of the cheap glyoxal, glutaraldehyde and terephthaldehyde (if desired by mixing these and, if desired, including a very limited amount of formaldehyde) can meet all likely needs in serving as a vital intermediate step in the conversion of the desirably structured known polyamide/(imide) membranes into "embrittlement resistant" membranes by further reaction with reactive phenols, proteins or other aldehyde-reactive substances. These can further form desirable derivatives for ultrafiltration, cross-flow filtration, ion-exchange, protein immobilization or packings for affinity chromatography. The vital point is that all of this can be done by immersion in suitable reagents whilst still retaining the carefully controlled initial porous structure.

Example 9

100 g. of a 60° C. dried polyamide 6 based membrane made according to Example 1 and containing 4% of reacted glutaraldehyde and 4% of reacted resorcinol based on the dry weight of polyamide membrane was heated 24 hours at 60° C. with 400 ml of a solution of 75 ml of 25% weight/volume glutaraldehyde and 40 g. of sodium benzoate buffer per liter. The original polyamide/glutaraldehyde reaction product contained only the equivalent of 1% of glutaraldehyde with a reactive single —CHO group as judged by rapid reaction with 2,4-dinitrophenylhydrazine. Furthermore the product was not stable to dilute acids, gradually releasing more aldehyde. However, by the present example it was possible to obtain the equivalent of 2% of single-linked glutaraldehyde which was now linked to a much more stable rubbery matrix. This doubling of the capacity to form derivatives is very important for ion-exchangers and ion-specific ultrafilters, eg: rejecting anionic detergents after treatment with bisulphite.

I claim:
1. A method of preparing a porous membrane comprising the steps of:
    (i) dissolving a thermoplastic polyamide or a thermoplastic polyamide/polyimide copolymer which has both relatively non-crystalline and relatively crystalline portions into a solvent under conditions of temperature and time which cause the relatively non-crystalline portions of the polyamide or copolymer to dissolve while at least a part of the relatively crystalline portions of the polyamide or copolymer do not dissolve, but form a colloidal dispersion in said solvent, wherein the said thermoplastic polyamide is a polyamide 6 or polyamide 6,6, and wherein the said polyamide/polyimide copolymer is a polyamide 6/polyimide copolymer or a polyamide 6,6/polyimide copolymer;
    (ii) forming said colloidal dispersion and solvent into a film and thereafter causing precipitation of at least part of the dissolved non-crystalline portions in the film to form a porous membrane matrix in which the pores are defined by spaces between the relatively crystalline portions, and,
    (iii) reacting the membrane matrix with an aldehyde as herein defined to link at least some of the relatively crystalline portions with the aldehyde.
2. A method according to claim 1 wherein the aldehyde is a bis-aldehyde.
3. A method according to claim 2 wherein the bis-aldehyde is glutaraldehyde, glyoxal, succindialdehyde, alpha-hydroxyadipaldehyde, terephthaldialdehyde or phthaldialdehyde or mixtures thereof.
4. A method according to claim 1 wherein the aldehyde is derived from a bis-aldehyde polymer, an acetal or an acetal ester.
5. A method according to claim 2 wherein aldehyde reaction step is so controlled that from 10% to 25% of the aldehyde chains are not linked at one end.
6. A method according to claim 5 including the step of reacting at least some of the free ends of the single-link aldehyde chains with a phenol.
7. A method according to claim 6 wherein the phenol is selected from the group comprising resorcinol, diphenylol propane, tannic acid, pyrogallol, hydroquinone, meta-cresol and naphthol as well as derivatives or mixtures thereof.
8. A method according to claim 5 including the step of reacting at least some of the free ends of the single-link chains with a protein or polyhydric colloid.
9. A method according to claim 5 including the steps of reacting at least some of the free ends of the single-link chains with gelatin or hydroxyethyl cellulose.
10. A method according to claim 6 including the step of reacting the phenol modified chain with sodium monochloroacetate in aqueous solution.
11. A method according to claim 6 including the step of reacting the phenol modified chain with aqueous diazonium salts.
12. A method according to claim 6 including the steps of:
    (a) reacting at least some of the remaining reactive single-link aldehyde chains with hydrazine,
    (b) reacting the phenolic hydroxyl groups with epichlorohydrin,
    (c) reacting the resultant epoxides with diamine to fix a pre-determined concentration of amine groups and hydrolyse excess epoxide to hydroxylsing, and,
    (d) reacting the amine groups with excess bis(isothiocyanate).
13. A method according to claim 6 and including the step of reacting the phenol modified membrane with a bis-aldehyde.
14. A method according to claims 1 to 5 wherein the membrane is reacted with sodium bisulphite, hydroxylamine-O-sulphonic acid or phenylhydrazinesulphonic acid.
15. A polymeric porous membrane prepared by a method comprising the steps of:
    (i) dissolving a thermoplastic polyamide or a thermoplastic polyamide/polyimide copolymer which has both relatively non-crystalline and relatively crystalline portions into a solvent under conditions of temperature and time which cause the relatively non-crystalline portions of the polyamide or copolymer to dissolve while at least a part of the relatively crystalline portions of the polyamide or copolymer do not dissolve, but form a colloidal dispersion in said solvent, wherein the said thermoplastic polyamide is a polyamide 6 or a polyamide 6,6, and wherein the said thermoplastic polyamide/polyimide copolymer is a polyamide 6/polyimide copolymer or a polyamide 6,6/polyimide copolymer, (ii) forming said colloidal dispersion and solvent into a film and thereafter causing precipitation of at least part of the dissolved non-crystalline portions in the film to form a porous membrane matrix in which the pores are defined by spaces between the relatively crystalline portions, and, (iii) reacting the membrane matrix with an aldehyde as herein defined to link at least some of the relatively crystalline portions with the aldehyde.

16. The polymeric porous membrane of claim 15, said polymeric porous membrane being made by using as the said aldehyde a bis-aldehyde.

17. The polymeric porous membrane of claim 16, said polymeric porous membrane being made by using as the said bis-aldehyde, glutaraldehyde, glyoxal, succindialdehyde, alpha-hydroxyadipaldehyde, terephthaldialdehyde or phthaldialdehyde or mixtures thereof.

18. The polymeric porous membrane of claim 15, said polymeric porous membrane being made by using as the said aldehyde an aldehyde derived from a bis-aldehyde polymer, an acetal or an acetal ester.

19. The polymeric porous membrane of claim 16, said polymeric porous membrane being made by controlling the aldehyde reaction step so that from 10% to 25% of the aldehyde chains are not linked at one end.

20. The polymeric porous membrane of claim 19, said polymeric porous membrane being made by reacting at least some of the free ends of the single-linked aldehyde chain with a phenol.

21. The polymeric porous membrane of claim 20, wherein the said polymeric porous membrane is made by using as the said phenol, resorcinol, diphenylol propane, tannic acid, pyrogallol, hydroquinone, metacresol and naphthol as well as derivatives or mixtures thereof.

22. The polymeric porous membrane of claim 19, said polymeric porous membrane being made by reacting at least some of the free ends of the single-link chains with a protein or polyhydric colloid.

23. The polymeric porous membrane of claim 19, said polymeric porous membrane being made by reacting at least some of the free ends of the single-link chains with gelatin or hydroxyethyl cellulose.

24. The polymeric porous membrane of claim 20, said polymeric porous membrane being made by reacting the phenol modified chain with sodium monochloroacetate in aqueous solution.

25. The polymeric porous membrane of claim 20, said polymeric porous membrane being made by reacting the phenol modified chain with aqueous diazonium salts.

26. The polymeric porous membrane of claim 20, said polymeric porous membrane being made by:

(a) reacting at least some of the remaining reactive single-link aldehyde chains with hydrazine, (b) reacting the phenolic hydroxyl groups with epichlorohydrin, (c) reacting the resultant epoxides with diamine to fix a pre-determined concentration of amine groups and hydrolyzing excess epoxide to hydroxyls, and, (d) reacting the amine group with excess bis(isothiocyanate).

27. The polymeric porous membrane of claim 20, said polymeric porous membrane being made by reacting the phenol modified membrane with a bis-aldehyde.

28. The polymeric porous membrane of claim 15, said polymeric porous membrane being made by reacting the membrane with sodium bisulfide, hydroxylamine-O sulfonic acid or phenylhydrazinesulfonic acid.

* * * * *